United States Patent [19]

Stein et al.

[11] Patent Number: 5,029,342
[45] Date of Patent: Jul. 9, 1991

[54] WELDER'S HELMET AND PHOTOVOLTAIC POWER TRANSMISSION CIRCUIT THEREFOR

[76] Inventors: Marc F. Stein, 10227 Rubin La., Philadelphia, Pa. 19116; Bradley O'Mara, 20255 Northglen Square, Cuppertino, Calif. 95014

[21] Appl. No.: 426,288

[22] Filed: Oct. 25, 1989

Related U.S. Application Data

[63] Continuation-in-part of Ser. No. 315,106, Feb. 24, 1989, abandoned, which is a continuation-in-part of Ser. No. 151,956, Feb. 3, 1988, abandoned.

[51] Int. Cl.$^5$ ............................................. A61F 9/06
[52] U.S. Cl. ............................................. 2/8; 2/171.3; 323/906; 290/1 R
[58] Field of Search ............................ 2/8, 171.3, 422; 323/906; 318/480; 307/140

[56] References Cited

U.S. PATENT DOCUMENTS

| | | | |
|---|---|---|---|
| 3,629,868 | 12/1971 | Greenlee | 2/8 X |
| 4,309,774 | 1/1982 | Guzowski | 2/8 |
| 4,468,569 | 8/1984 | Norris | 323/906 X |

*Primary Examiner*—Peter Nerbun
*Attorney, Agent, or Firm*—Donald C. Simpson

[57] ABSTRACT

A welder's helmet including a panel of solar cells responsive to light generated by a welding operation to drive a fan incorporated in the helmet structure. The solar cells are mounted on the helmet above the viewing window and the fan is mounted in front of the mask below the viewing window. When a welding arc is struck, the light from the torch impinges on the solar panel and generates sufficient electricity to drive the fan. The fan forces air from the inside of the helmet outward through the front face in a velocity controlled stream carefully directed to prevent smoke and fumes from reaching the helmet, and to also blow the smoke away from the weld site in a particular manner so that visibility of the weld remains clear while not over-oxygenating the weld site. As air is exhausted from the inside of the helmet outward by the fan, fresh air is drawn in around the sides to replace that which is being exhausted to cool the welder and prevent ingestion of fumes and vapors. A photovoltaic power transmission circuit is provided to process electrical energy derived from light such as that produced by the arc of an arc welder during a welding operation.

8 Claims, 8 Drawing Sheets

FIG. 13
ELEV. A-A

FIG. 14

WELDER'S HELMET AND PHOTOVOLTAIC POWER TRANSMISSION CIRCUIT THEREFOR

This patent application is a continuation-in-part of co-pending patent application Ser. No. 07/315,106 filed Feb. 24, 1989, now abandoned which was a continuation-in-part of patent application Ser. No. 07/151,956 filed Feb. 3, 1988, now abandoned.

This generally to welder's helmets, and more particularly relates to a welder's helmet having incorporated therein means for improving the visibility of the welding site during a welding operation.

In the past, welding helmets have been known which utilize a self-contained power source to draw air into the inside of a welding helmet through a filter and to exhaust the air from the helmet, the purpose of such device being to prevent the gases and smoke from the welding work area from moving up behind the front of the welding helmet and to the nose and eyes of the welder. It is also known to use a blower to clear smoke directly from the welding site. While helmets of this type provide some improvement over helmets not incorporating these features, nevertheless some problems remain, and the present invention is directed toward overcoming the shortcomings and to thereby provide a fully functional improved welder's helmet.

The welder's helmet, according to the invention, includes a panel of solar cells or photovoltaic (the terms are used interchangeably herein) responsive to the light generated by a welding operation to drive a small fan or blower which is incorporated into the helmet structure. The solar cells are mounted on the helmet above or below the viewing window and the fan is mounted in front of the mask above or below the viewing window. During a welding operation, when the welding arc is struck for carrying out the welding operation, the light from the torch before and during welding impinges on the solar panel and generates sufficient electricity to drive the fan.

The fan forces air from the inside of the mask or helmet outward through the front face of the mask in a stream which is carefully directed to prevent smoke and fumes from the welding operation from reaching the mask, and is also so directed and of sufficient force to blow the smoke away from the weld site so that visibility of the welder remains clear. As air is exhausted from the inside of the mask outward by the fan, fresh air is drawn in around the rear and sides of the mask to replace that which is being exhausted, and thus helps to cool the welder and also to prevent ingestion of noxious fumes and vapors.

Some kinds of welding produce substantially more smoke and light than other conditions, and in such circumstances a higher volume of air is required to clear the weld area for visibility. However, it is not helpful to provide more air than is necessary to clear the smoke because an excess of air, if it impinges on the weld site, can interfere with the welding process by causing too much oxygen to appear at the weld site. For that reason, it is best to utilize no more air than is absolutely necessary to provide proper vision at the weld site, and it is, therefore, desirable to have the air speed from the fan under the control of the welder.

For this purpose, three different fan speed control devices are utilizable with the helmet, either singly or in combination if so desired. In one case, a variable resistance is incorporated in series with the solar cell array and the fan motor to control the current and voltage to the motor, and therefore, control the fan speed another control is the incorporation of an aperture control placed in front of the solar cell array to effectively control the amount of light permitted to reach the array from the weld site and, therefore, to control the voltage and current output of the solar cells, which in turn controls the speed of the fan motor. A third possible control is one which controls the angle made by incident light from the weld site with the plane of the solar cells array.

Additionally, incorporated into the helmet structure are spatter control devices in the form of transparent replaceable panels disposed in front of the viewing window and in front of the solar cell array.

Photovoltaic cells for converting light energy into electrical energy are known in the art. Conventionally these photovoltaic cells generate direct current electricity from light, for example, from sunlight. The higher the intensity of the light source, the greater the amount of power that will be produced by the photovoltaic cell.

Photovoltaic cells, like the human eye, respond differently to different wavelengths of light. Both natural light (e.g. sunlight) and artificial light (e.g. fluorescent light) are suitable light sources for generating power using photovoltaic cells. However, photovoltaic cells require a relatively constant intensity light source to generate and supply electricity at a constant current and/or voltage necessary for most electrical loads (e.g. motors, electronic circuits, et cetera) to function efficiently.

The light produced by an arc welder during a welding operation varies in intensity over a wide range and at a rapid rate. This light, when applied to a photovoltaic cell, will produce a relatively inconsistent and erratic current as compared to the current produced from standard light sources, for example, sunlight. Additionally, the current produced is extremely variable in amplitude as a function of the intensity of the arc. U.S. Pat. No. 3,238,535 to Richev and U.S. Pat. No. 4,309,774 to Guzowski disclose the concept of powering a motor using photovoltaic cells powered by the light of, inter alia, an arc welder during a welding operation. Both Richey and Guzowski teach connecting the photovoltaic cells directly to the motor to be driven. Because of the variable nature of the light from an arc welder, a photovoltaic cell connected directly to a device as taught by Richev and Guzowski cannot produce electricity of a constant current level when it has an arc welder or other variable source as a source of energy. This makes it virtually impossible to efficiently drive devices that require a relatively constant current to operate, for example, electric motors, directly from the photovoltaic power source.

A second problem exists when using a photovoltaic system as taught by Richev or Guzowski. An impedance mismatch exists between standard motors and photovoltaic cells, resulting in each attempting to force the other to operate at different voltages and currents than they are designed for. The greatest mismatch occurs when a DC motor's start-up current exceeds the current available from the photovoltaic cell. This mismatch results in a stalled motor and thus no rotation even under exposure to light levels that are high enough to sustain motor rotation if the motor were already running. Thus, the only way for the photovoltaic cell to operate the motor is if the motor has some kind of start-up assistance, either manual or electrical. Once running, the impedance mismatch continues, improperly loading the photovoltaic cell, causing it to deliver less power than it is capable of delivering. This results in low motor speed and inefficient operation.

Accordingly, it is a primary object of the invention to provide a novel welder's helmet including a fan or a blower so mounted to the helmet as to produce a smoke clearing air stream focused at approximately four to five inches above the welding site to clear the smoke therefrom without over-oxygenating the active welding location.

Another object of the invention is to provide a novel welder's helmet as aforesaid including self-contained power generating means for energizing the fan or blower. Yet another object of the invention is to provide a novel welder's helmet as aforesaid including a fan speed control operable by the wearer of the helmet so that precisely the correct air stream is generated for a particular welding circumstance.

It is also an object of this invention to provide a photovoltaic power transmission circuit which efficiently extracts and processes the maximum electricity available/producible from a photovoltaic generator and delivers the electricity to an electrical device at such current and voltage levels which allow for its efficient operation.

It is still another object of this invention to provide a photovoltaic power transmission circuit which efficiently extracts and processes electricity from the light generated by a welding torch during a welding operation, the electricity delivered to the load being of a current level within a predetermined range.

It is a further object of this invention to provide a photovoltaic power transmission circuit which efficiently extracts and processes electricity from the light generated by an arc welder during a welding operation and which does not require manual start-up assistance to being operation of the motor.

The foregoing and other objects of the invention will become clear from a reading of the following specification in conjunction with an examination of the appended drawings, wherein.

In the several figures like elements are denoted by like reference characters.

Figure 1:
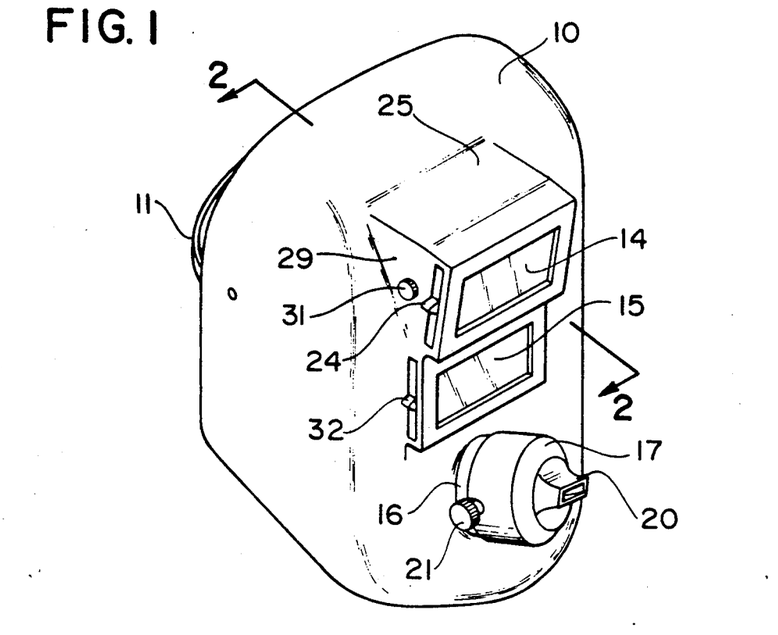
FIG. 1 is an isometric view of the welder's helmet according to the invention as viewed from the front and above at one side.
Figure 2:
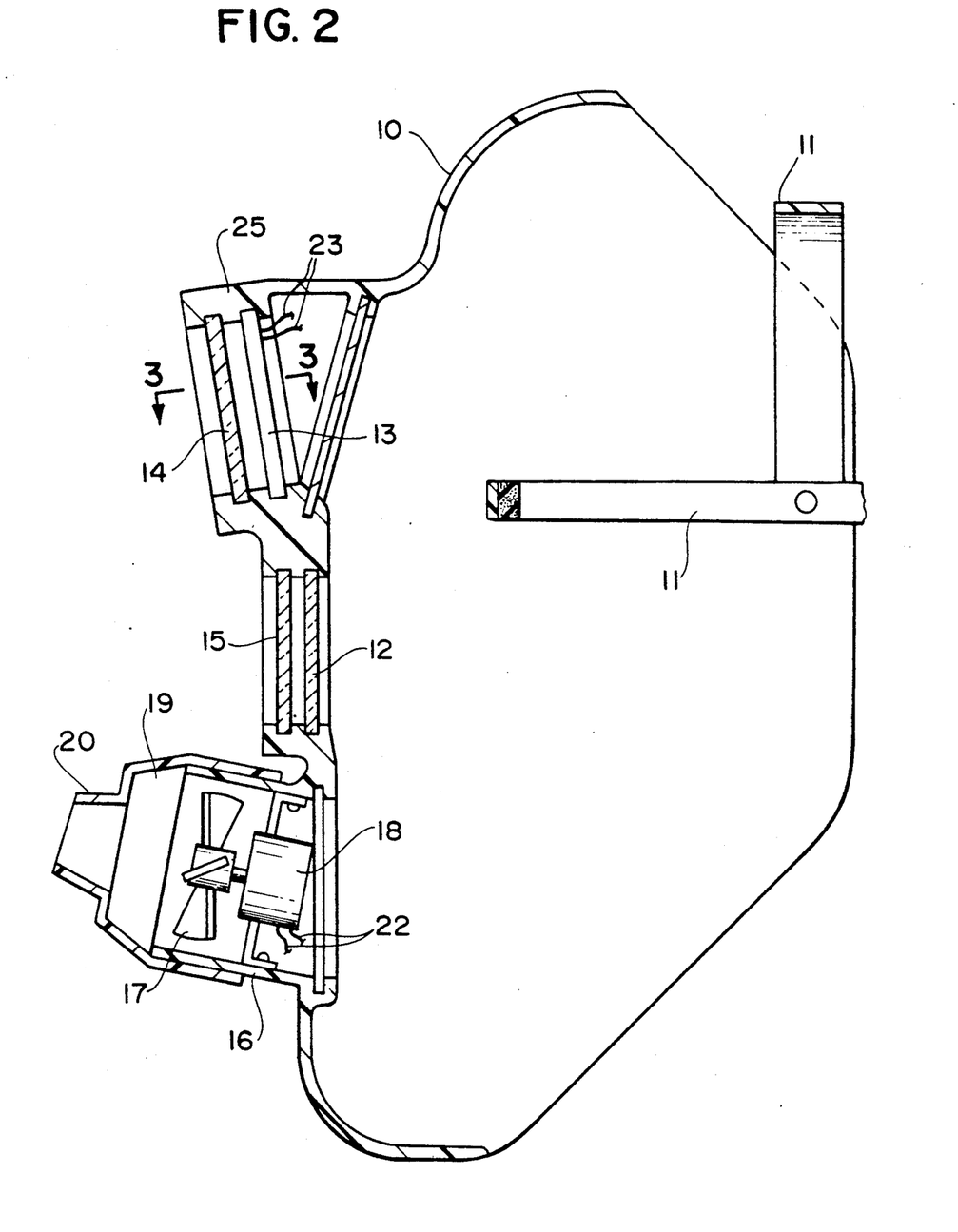
FIG. 2 is a vertical section on an enlarged scale through the helmet of FIG. 1 as would be seen when viewed along the line 2—2 of FIG. 1.

Turning now to a consideration of the drawings, and firstly FIGS. 1 and 2, there is seen a welder's helmet designated generally as 10, including conventional head mounting straps 11 and a conventional viewing window 12. Mounted in the front of the helmet above the viewing window 12 is a solar cell array 13, having disposed in front of it a protective shield 14 which may be similar to the protective shield 15 disposed in front of the viewing window 12. Positioned on the front of the helmet below the viewing window 12, is a tubular formation 16 within which is mounted an electrically driven fan or blower including the fan blade 17 and driving motor 18, as best seen in the showing of FIG. 2. Removably projected onto and fitting snugly to the tubular formation 16 is an airstream controller 19 having an angled and shaped air director 20 which controls the shape and direction of the airstream generated by the fan or blower. Also mounted to the tubular formation, as best, seen in FIG. 1, is a small electrical rheostat 21 which is connected in series with the fan motor 18 and solar cell array 13 by means of the conductors 22 and 23 respectively to thereby control the fan speed.

Figure 3:
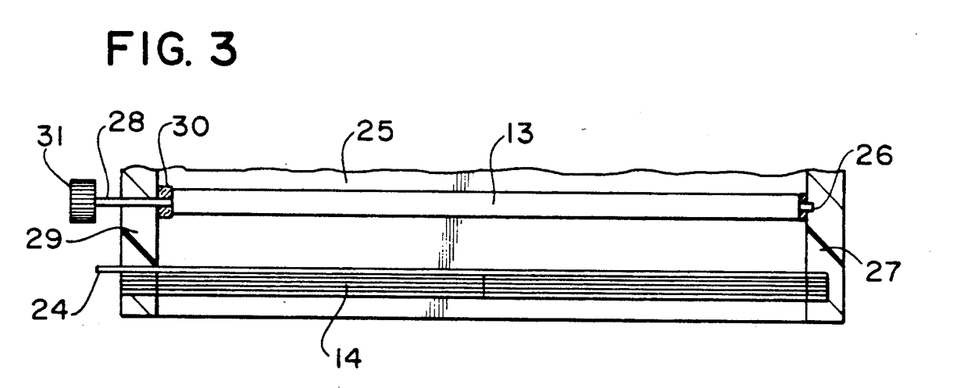
FIG. 3 is a horizontal sectional view through the solar cell array and protective device as would be seen when viewed along the line 3—3 on FIG. 2.

As best seen in FIG. 3, the protective shield 14 disposed in front of the solar cell array 13 consists of a packet of stacked transparent plastic pieces removably secured to one another along one rectangular edge of each layer, and having an externally projecting finger tab 24 by means of which the entire protective shield pack 14 may be slipped laterally out of the housing 25 within which the solar cell array 13 and protective shield 14 are disposed so that the outermost layer of the protective shield may be torn off and discarded and the protective shield pad then reinstalled in its position before the solar cell array. This is necessary because during welding operations eventually weld spatter will strike the protective pad and eventually cause impairment of light transmission to the solar cell array. Similarly, the protective shield 15 disposed in front of the viewing window 12 is provided with a finger tab 32 for exactly the same purpose of the finger tab 24 just described.

If desired, the solar cells array may be made to be rotatable within an angle of approximately sixty degrees about an axis lying in the plane of the array in order to control the effective surface of the array incident to light from a welding site, and thereby control the electricity generated by the array. A simple system for effecting this result is shown in FIG. 3. The right end of solar cells array 13 is fitted with a pivot pin 26 journaled in a socket formed in the sidewall 27 of housing 25, while the left end of the array is provided with a cylindrical shaft 28 which passes through an aperture in the other sidewall 29 of housing 25. Compressed between the end of the array 13 and housing sidewall 29 is a friction washer 30 which holds the array in whatever position it is set by rotation of the knob 31 secured at the end of shaft 28.

Figure 4:
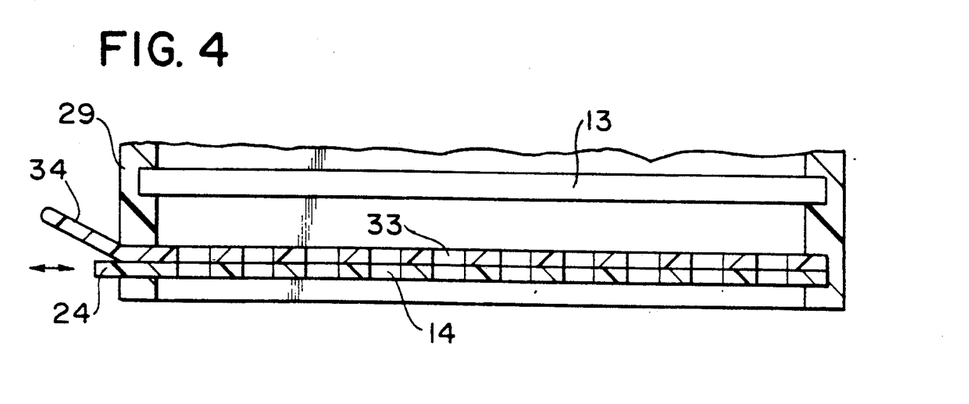
FIG. 4 is a view similar to FIG. 3, but showing a modified structure incorporating a light control device.

FIG. 4 shows a structure similar to that shown in FIG. 3, but including one additional part, which is an opaque or semi-opaque slideable light shield designated generally as 33 and having a finger graspable handle 34. The light shield 33 may be utilized in place of the rheostat 21 since it can provide the same function. In operation, the shield 33 is slid laterally by means of the handle 34 to expose more or less of the solar cell array 13 and thereby control the effective amount of light impinging on the solar array. This in turn controls the electrical power generated by the solar cell array, and thereby controls the speed of the fan 17.

Figure 5:
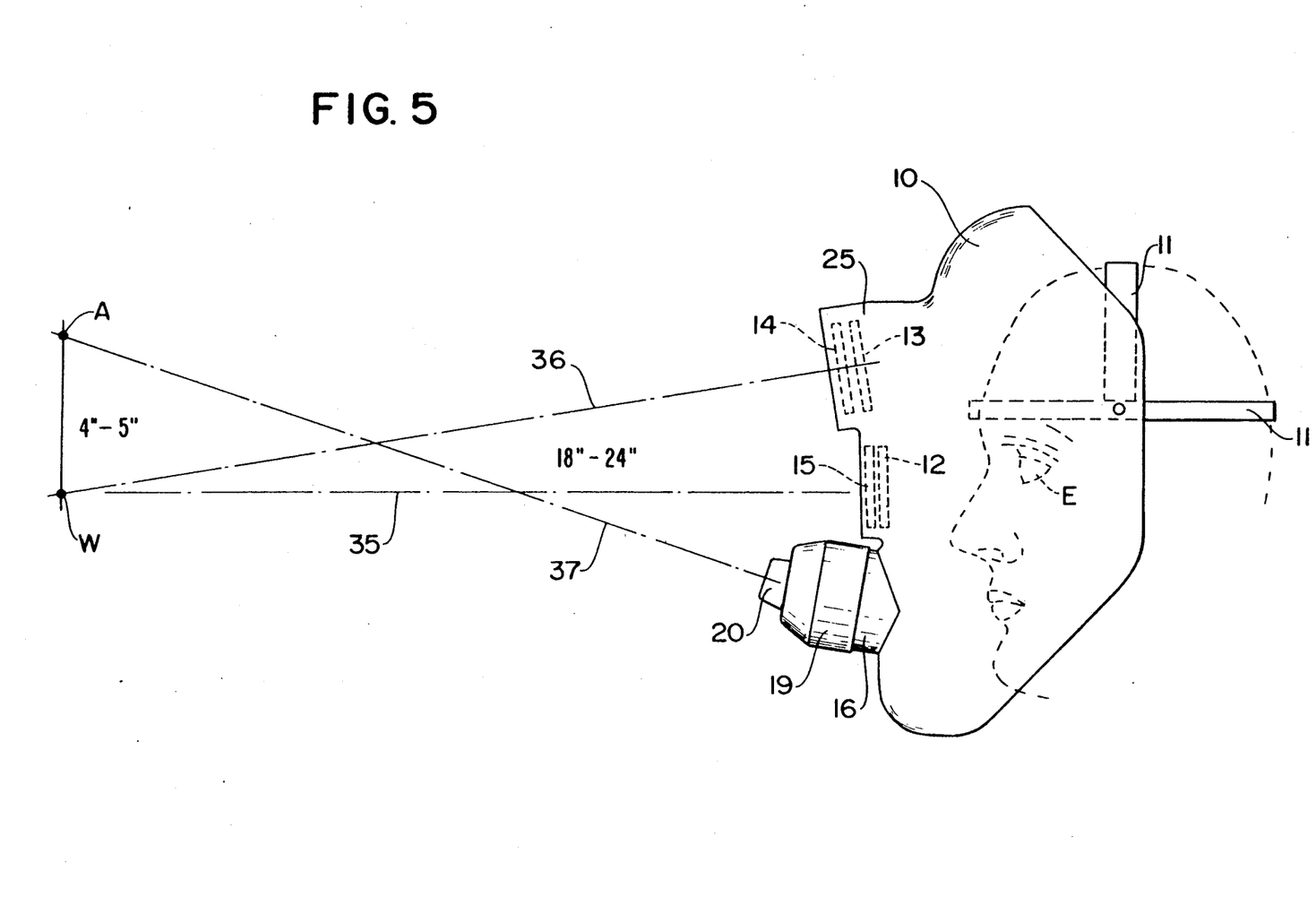
FIG. 5 is a diagrammatic side view of the novel welder's helmet according to the invention in use and illustrating the lines of incident vision for the welder, the light from the weld site to the solar array, and the flow path of air from the fan or blower.

Consider now the diagrammatic showing of FIG. 5. This figure shows the effective operating parameters of the various devices incorporated into the welder's helmet according to the invention. The normal welding distance between the weld site W and the eye of the welder E is usually in the range of eighteen inches to twenty-four inches, and this is shown by the line of sight 35 in FIG. 5. The housing 25 within which the solar cell array 13 is angled so that the line 36 orthogonal to the plane of the solar cell array also passes through the welding site designated as the point W. The tubular formation 16 and airstream controller 19 are formed to the helmet 10 at such an angle that the airstream controller 19 with the air director 20 is capable of directing the airstream along the axial line 37 so that the airstream effectively reaches the location of the weld site at the point A which is substantially 4 inches to 5 inches above the weld site W. This prevents direct impingement of the air on the weld site and avoids over-oxygenation of the weld location while still very effectively removing the smoke and gases from the weld area. The welder, of course, controls the airstream velocity by means of either the rheostat 21, the knob 31 or the light shield 33, whichever is incorporated into the structure. The airstream controller 19 can, of course, be made in various configurations to achieve particular controlled airstream configurations.

The embodiments shown in FIGS. 1 through 5 present the welding helmet with the solar cells mounted above the viewing window and the fan located below the viewing window. In fact, however, these positions can be reversed or modified to provide other types of air distribution. Thus, for example, in the embodiment shown in FIGS. 6 through 8, the solar panel has been placed below the viewing window and the blowing has been directed completely within the internal system of the welding mask to maximize the presentation of clean air and cooling to the user. Other variations of these embodiments will be obvious to those ordinarily skilled in the art.

Figure 6:
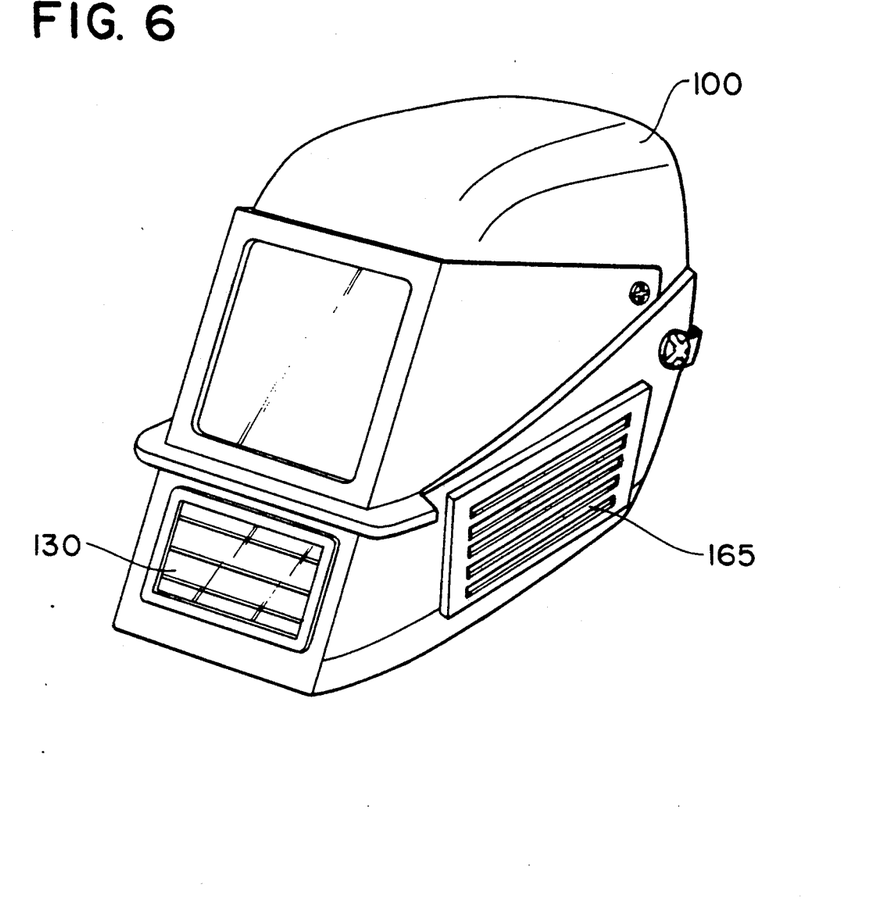
FIG. 6 is an isometric view of a preferred embodiment of the welder's helmet according to the invention.
Figure 7:
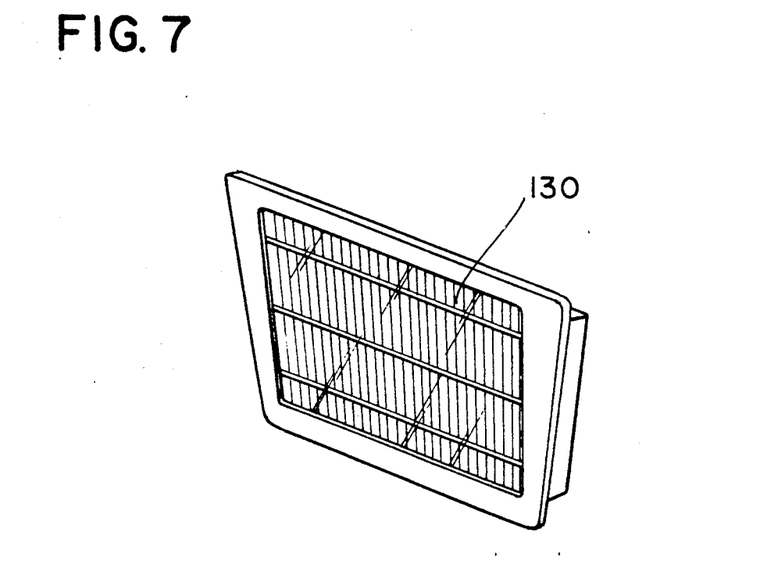
FIG. 7 is an isometric view of the solar cell insert for the welder's helmet of FIG. 6.
Figure 8:
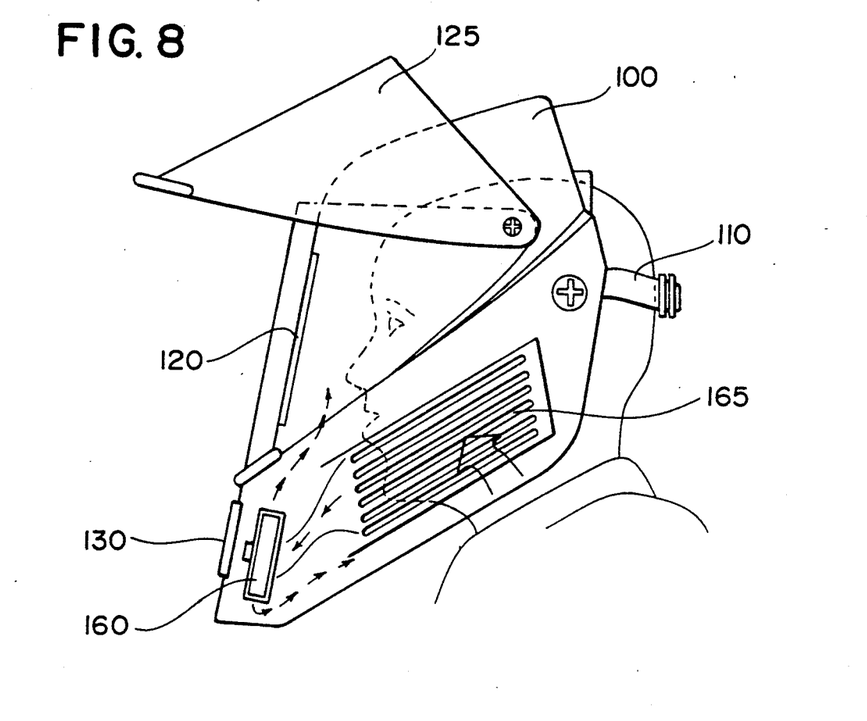
FIG. 8 is a horizontal side elevation of the welding helmet of FIG. 6 in partial section, particularly noting the manner of air flow and the internal location of certain specific parts.

For convenience in following the descriptions, in FIGS. 6 through 8, those parts which correspond generally to parts found in the embodiment of FIGS. 1 through 5 have been identified by the same numbers as in the first five drawings, except multiplied by 10. Parts not finding counterpart in FIGS. 1 through 5 will, of course, have their own separate numbers. Welding helmet 100 is provided with supporting strap 110, conventional viewing window 120, and solar array 130. The embodiment shown in FIG. 8 is further provided with a transparent splatter shield which is easily replaced and can be raised and lowered over the principal viewing window during normal use. The solar cell array 130 can be made rotatable to maximize or minimize energy input much as was described for solar array 13 in the embodiment of FIGS. 1 through 5. Tubular formation 160 contains appropriate fan and motor with diverters for sending air received through side vents 165 for general distribution throughout the interior of the helmet. If desired, additional tubular outlets could be provided to permit blowing external to the helmet in the general area of the weld operation. The air is drawn through suitable filtration media known in the art.

The foregoing welding helmet provides a significant improvement of those of the prior art described previously. However, all of the foregoing welder's helmets of the prior art and the present welding helmet are subject to variations in the power output from the photovoltaic power source. Accordingly, a few transmission circuit was developed to overcome these problems.

The new photovoltaic power transmission circuit comprises:
(1) Light source means for generating light energy;
(2) Photovoltaic power means for producing electrical energy, having a voltage current and power, from light energy generated by said light source;
(3) Electrical device means for consuming the electrical energy produced by said photovoltaic power means;
(4) Switch means for connecting said electrical device means to said photovoltaic power means when said switch means is energized and for disconnecting said electrical device means from said photovoltaic power means when said switch means is de-energized;
(5) Reference voltage means for outputting a reference voltage;
(6) Comparing means for comparing the reference voltage with the voltage produced by said photovoltaic power means and providing first and second output signals to said switching means, said first signal energizing said switch means and said second signal de-energizing said switch means.

Figure 9:
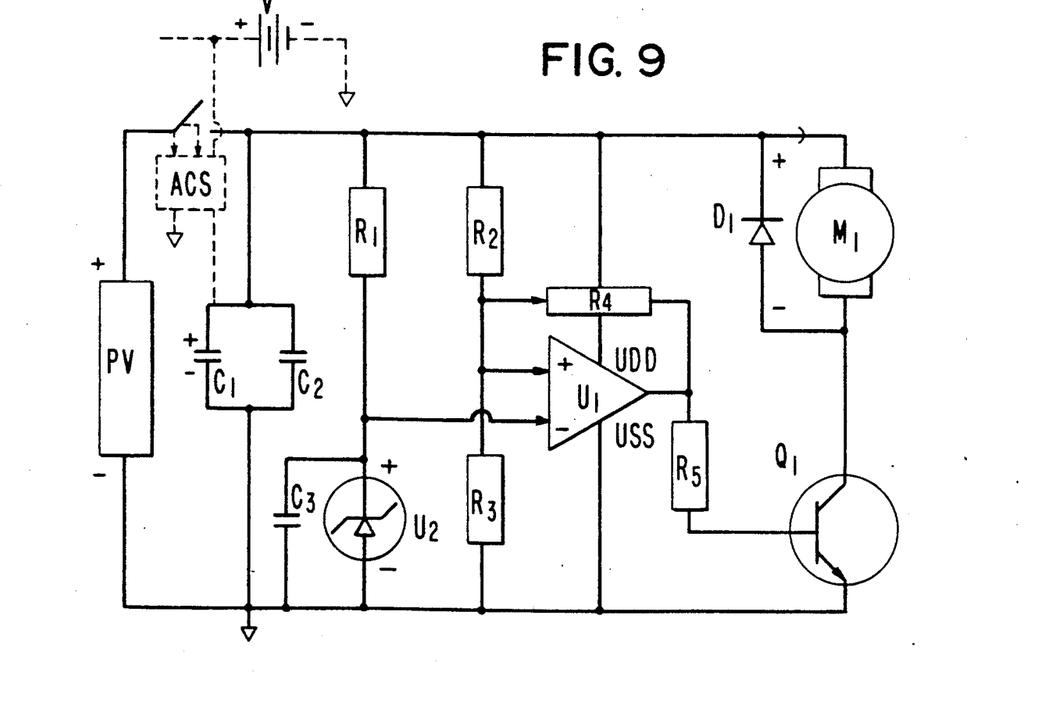
FIG. 9 is a schematic diagram of a power transmission circuit according to the present invention.

FIG. 9 is a schematic diagram of a power transmission circuit according to the present invention. A photovoltaic panel PV is coupled via ON/OFF switch S1 across parallel connected capacitors C1 and C2. Photovoltaic panel PV and capacitors C1 and C2 comprise a photovoltaic power means. Photovoltaic panel PV can comprise, for example, a single crystal 4"×4" panel produced by ARCO Solar, Inc., having a 0.484 volts peak power point rating @2.7 amperes under full sun exposure. The panel can be cut into 8 equal area cells that are series connected and epoxy encapsulated with one set of leads emerging from the panel. Capacitor C1 can comprise, for example, a 200 micro Farad, 6 volt electrolytic capacitor. Capacitor C2 operates as a high frequency switching filter and can comprise, for example, a 0.10 micro Farad, 25 volt metalized film capacitor.

When switch S1 is closed and photovoltaic panel PV is exposed to a light source, capacitor C1 begins to charge. A comparator U1 (e.g., an LM224 operational amplifier) compares a voltage across a voltage divider, comprising resistors R2 and R3, with a reference voltage supplied by a reference voltage source U2 (e.g., an ICL8069 1.2 volt band-gap voltage reference IC made by Intersil Corporation). Capacitor C3 operates as a noise filter and oscillation stabilizer for U2 and can comprise, for example, a 0.10 micro farad, 25 volt metalized film capacitor. R1 operates as a current limiting means to power U2 and can comprise, for example a 10,000 ohm, ⅛ watt, 5% tolerance resistor. Comparator U1, the R2, R3 voltage divider, and voltage source U2 comprise a comparing means. The voltage across the R2, R3 voltage divider is a function of the voltage across capacitor C1. Resistor R2 can comprise, for example, a 150,000 ohm, ⅛ watt, 5% tolerance resistor. Resistor R3 can comprise, for example, a 100,000 ohm, ⅛ watt, 5% tolerance resistor.

Resistor R4 (e.g., a 1,000,000 ohm, ⅛ watt, 5% tolerance resistor) is coupled between the output OP1 and the plus (+) input of comparator U1. This connection sets a "hysteresis window" for comparator U1. This window causes the output of comparator U1 to be of a first level, e.g. a logic "1", when the voltage across capacitor C1 goes above a predetermined discharge threshold level (e.g. 5% higher than the maximum power voltage of the photovoltaic panel PV), and causes the output to be of a second level, e.g. a logic "0", when the voltage across capacitor C1 drops below a second predetermined charge threshold level (e.g. 5% below the maximum power voltage of the photovoltaic panel PV).

The output of comparator U1 is coupled to a transistor Q1 (e.g., a 2N4401 NPN silicon bipolar transistor) via resistor R5 (e.g., a 100 ohm, ⅛ watt, 5% tolerance resistor which serves as a current limiting means to supply bias current to the base terminal of transistor Q. Motor M1 (e.g., a Mabuchi RF-510T-26 DC permanent magnet motor) has its positive terminal connected to the positive terminal of the capacitor C1. The ground terminal (−) of motor M1 is connected to the collector of transistor Q1. Thus, when the switch S1 is closed and the transistor Q1 is energized, a complete circuit is created, linking the motor M1 to photovoltaic panel PV and capacitor C1.

The operation of the circuit of FIG. 9 utilizing, as an example, the light from the arc of an arc welder to energize the photovoltaic panel PV is described below. With switch S1 closed, the arc is struck by the welder. Capacitor C1 begins to charge until it reaches a voltage that exceeds the charge threshold of the comparator, for example, a voltage 5% higher than the maximum power voltage needed to power motor M1. As the voltage exceeds the charge threshold, the state of the output of comparator U1 switches, sending a bias current to the base of transistor Q1 via resistor R5. This energizes transistor Q1, connecting the motor M1 across photovoltaic power means. Since the motor M1 draws a current that is in excess of that which can be supplied by the photovoltaic panel PV, capacitor C1 begins to discharge current as it is drawn by the motor M1. The voltage across capacitor C1 begins to drop until it drops below the discharge threshold, at which point the state of the output of comparator U1 switches back to the first state, cutting off the bias current to the base of transistor Q1. This terminates the current to the motor M1 from the photovoltaic cell PV and capacitor C1. The capacitor C1 then begins to recharge, and continues charging until it reaches the charge threshold at which point the output of comparator U1 again changes to the second state, energizing transistor Q1 and beginning the cycle again. This cycle continues to repeat as long as the arc is struck.

Diode D1 is a flywheel diode which maintains conduction of current through motor M1, in a well known manner, during the period that transistor Q1 is not energized and the capacitor C1 is charging.

In a preferred embodiment, there is also provided an active current switch, ACS, and rechargeable battery, V. These serve as means to store electricity available from the photovoltaic generator during periods of non-use of motor M, (i.e. when welding shield is not worn/used, but is still exposed to light, such as sunlight, window/diffused light or indoor/home/shop light.) The ACS acts as a constant current converter capable of re-routing only as much current as is necessary to operate said motor at a predetermined rote and for a predetermined length of time, such as may be useful to provide the welding operator a continuous flow of clean filtered air after arc usage has stopped, but during which time considerable amounts of particulate matter still permeate the breathing space and air around the welder.

Figure 10:
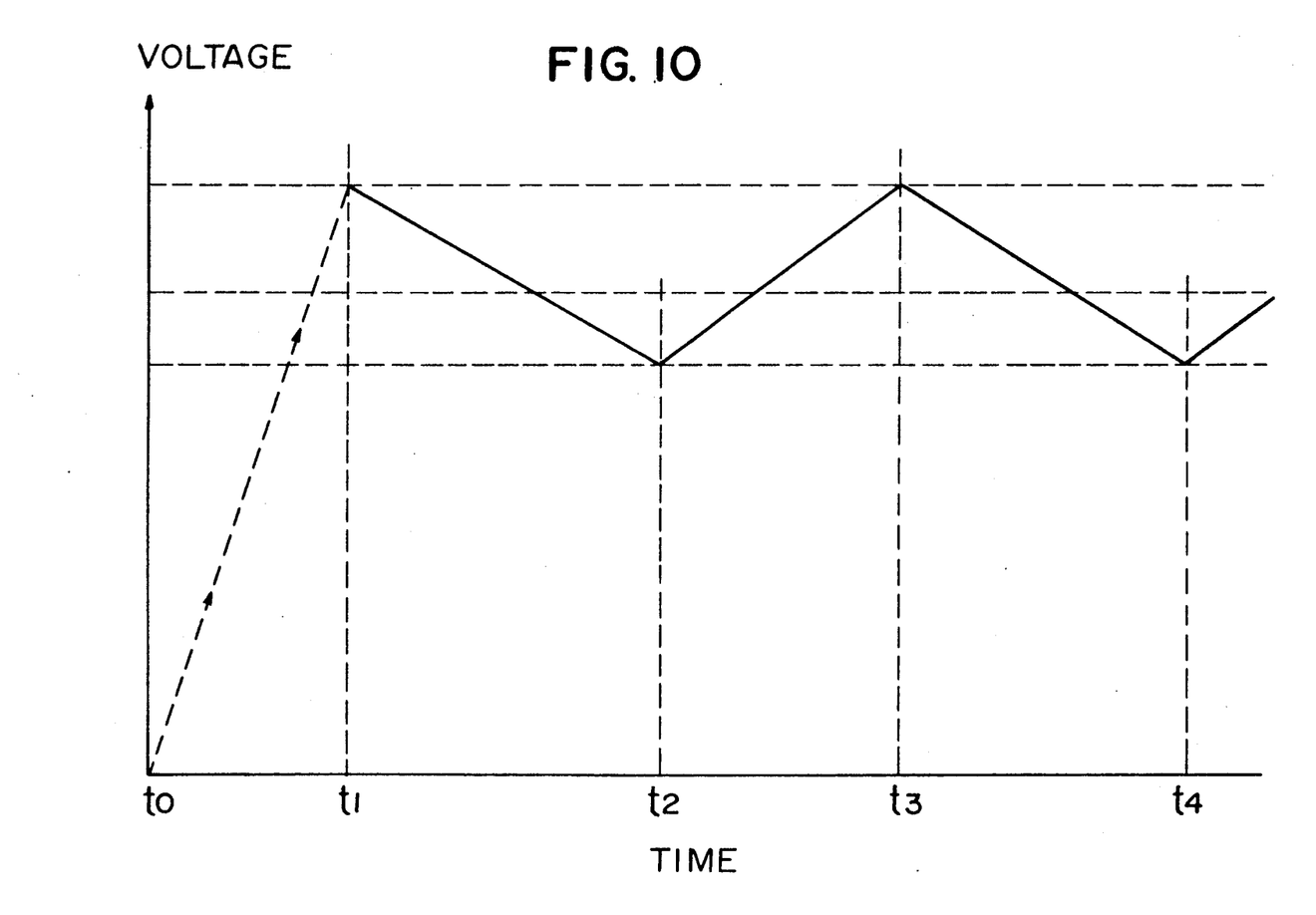
FIG. 10 is a graph of the charge/discharge cycle of the power transmission circuit of FIG. 9.
Figure 11:
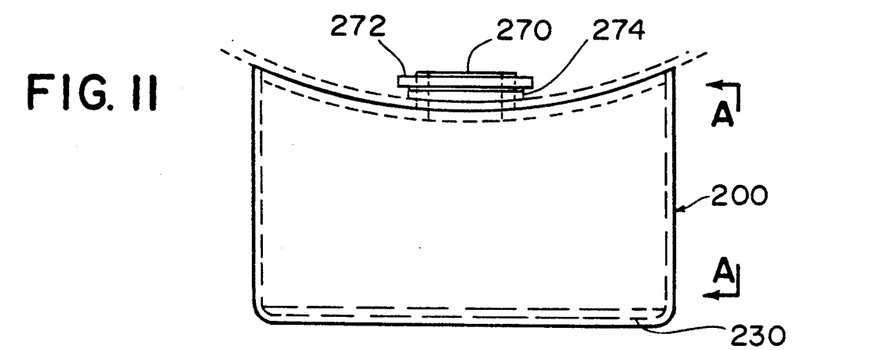
FIG. 11 is a top view of a filtering unit which can be separately mounted on any welding mask.
Figure 12:
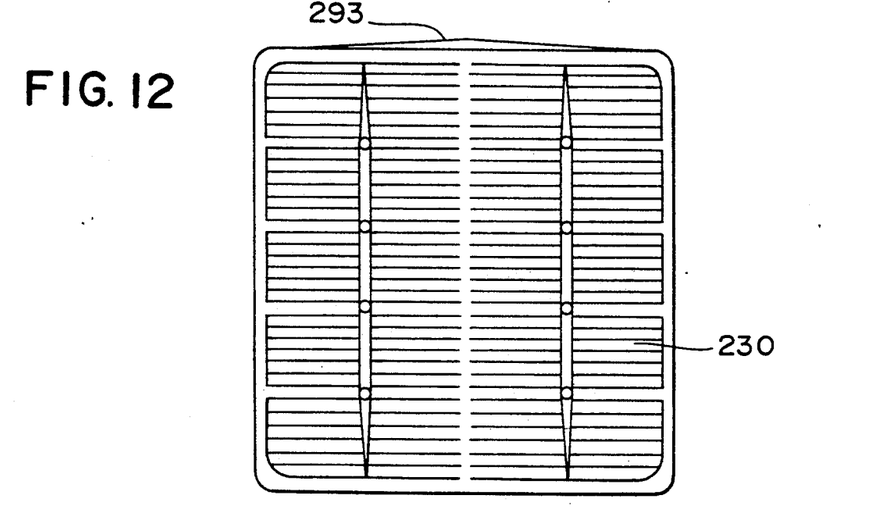
FIG. 12 is a front elevation of the separate unit of FIG. 11, showing in particular the solar unit.
Figure 13:
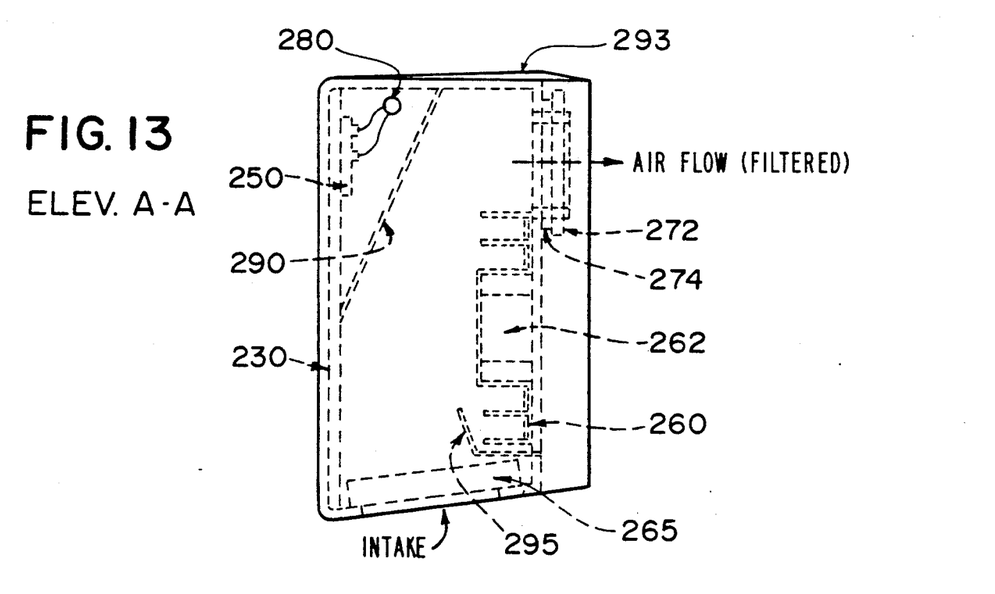
FIG. 13 is a side elevation from the view A—A of FIG. 11 with internal components shown in phantom lines.

FIG. 10 is a graph showing the voltage across the capacitor C1 during operation of the power transmission circuit. At time $t=0$, there is no voltage across the capacitor C1. This represents the point at which the photovoltaic panel PV is not being energized by light. Between $t=0$ and $t=1$, the arc has been struck, energizing the photovoltaic panel PV. The voltage across capacitor C1 increases until it reaches the charge threshold, at which point transistor Q1 is energized (time $t=1$). When transistor Q1 is energized, the motor M1 begins to operate, discharging the capacitor C1, as shown during time $t=1$ to $t=2$. At time $t=2$, the voltage across capacitor C1 reaches the discharge threshold. At this point, the transistor Q1 becomes de-energized, disconnecting motor M1 from the circuit. At this point, the capacitor C1 begins the recharge cycle ($t=2$ to $t=3$). While the capacitor C1 is recharging the motor M1 free-wheels, because it is disconnected from the energy source. The charge/recharge cycle occurs at a high rate of speed, and the induction of the motor windings smooths out any variations of current due to this cycling. Thus, the current through the motor M1 is maintained at a constant level.

During and throughout this charge/discharge process, it is apparent from FIG. 10 that the voltage seen across capacitor C and, thus, the voltage at which the photovoltaic generator operates approaches very closely the ideal voltage at which 100% maximum power is extracted from the photovoltaic generator's maximum power voltage. Because the charge and discharge threshold voltages at which the motor M is switched "on" and "off" of the photovoltaic/capacitor C, circuit are both independently set via appropriate selection of the ohmage valves of resistors R2, R3 and R4, it is possible to utilize this power transmission circuit invention in a wide variety of photovoltaic generator, light level, and motor load applications across a wide range of power levels. In essence, this invention allows for the efficient, practical and cost-effective use of photovoltaic generators exposed to welding arc light sources for applications other than said air respirator design.

It is important to note that achieving maximum power extraction from a photovoltaic generator under conditions of erratic, nonregular and discontinuous light levels, such as is described here from a welding arc light source, has until now not been practically feasible due to the extremely sophisticated and costly circuitry otherwise required to electronically load the photovoltaic generator at or near its maximum power voltage.

This sophistication has heretofore been necessary to measure, compute, track, and "remember" via solid-state memory circuits, where the photovoltaic generator is being operated.

Said invention then serves in essence as (1) a maximum power extraction device to obtain the maximum available power from the photovoltaic generator, under/over a very wide dynamic range (10:1 or more); and (2) a constant power pump/source to force this extracted power into a motor load device, regardless of said motor's actual voltage current/imedance characteristics. Said invention then acts to instantaneously and continually, 1,000 times per second or more, actively re-adjust its "loading" of the photovoltaic generator to insure it is being operated at, or very near, its maximum power voltage so as to extract the maximum practical power available, and then to "force" or re-form said power into whatever voltage-current combination results in said power being consumed by the motor load device, regardless of the motor's otherwise mismatched impedance.

Figure 14:
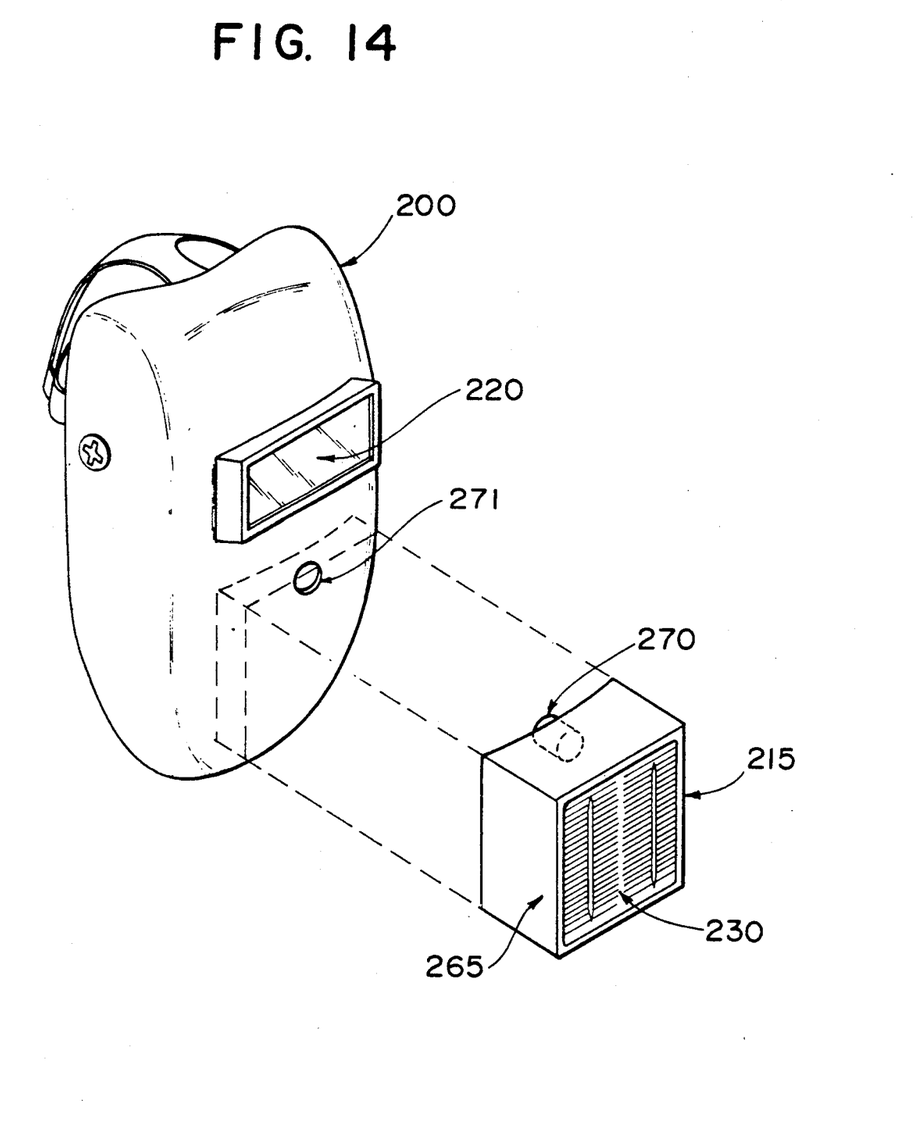
FIG. 14 is an isometric view of a welding mask, showing the method of fixing the portable separate unit to the welding mask.

In the foregoing description, the invention is described in terms of a welding mask with built-in filtering unit. In a preferred embodiment, however, the filtering unit is a separate unit which is attachable to essentially any standardized welding mask. The attachable unit is illustrated in FIGS. 11 through 14. As shown in FIG. 14, there is provided an attachable filtration unit 215 which may be affixed to a welding mask 200 through hole 271 which may be bored into the mask underneath the welding glass 220. As shown in the detailed drawings of FIGS. 11 through 13, attachable filtration unit 215 has a tubular member 270 which passes into the opening 271 in the mask and can then be affixed in place by way of lock nut 272. Air is sealed between the unit with an appropriate O-ring 274. The unit comprises a housing made of a suitable polycarbonate-ABS plastic injection molded material. A photovoltaic panel is provided at 230. As shown in the preferred embodiment, this is a 4.5 VDC/250 milliamp 10 cell single crystal photovoltaic panel using epoxy encapsulent with ABS substrat. A power control board 250 can be positioned in the upper portion of the unit and protected by an appropriate barrier and deflector 290. An optional alternative electrical source, battery 280, may be provided. The system is also provided with a windscreen, 295, which, together with the barrier and deflector, can control the flow of air within the unit and insure that various elements of the unit are properly protected. The air flow is controlled by a suitable turbine blade 260 with motor 262 and the filtration unit 265 may be an activated charcoal filter media.

Referring again to the circuit schematic of FIG. 9, the preferred attachable unit comprises the following:

| | |
|---|---|
| PV | Solar panel, 10 cells, each 5 H 1 cm., CZ. |
| C1 | 150 micro Farad, 6 volt electrolytic capacitor. |
| C2,3 | 0.10 micro Farad 25 volt metallized film capacitor. |
| R1 | 10,000 ohms, ⅛ watt, 5% tolerance. |
| R2 | 180,000 ohms, ⅛ watt, 5% tolerance. |
| R3 | 100,000 ohms, ⅛ watt, 5% tolerance. |
| R4 | 1,000,000 ohms, ⅛ watt, 5% tolerance. |
| R5 | 100 ohms, ⅛ watt, 5% tolerance. |
| U1 | LM358 operational amplifier IC, 8 pin mini-dip package. |
| U2 | ICL8069 1.2 volt band gap voltage reference IC. |
| D1 | 1N5817 hot carrier Schottky diode, 1 amp/20 volt. |
| M1 | DC permanent magnet motor, Mabuchi RF-510T-18315. |
| Q1 | Transistor, 2N4401 NPN silicon bipolar. |

This embodiment permits production of a smaller, lighter weight unit, which is more easily attached to existing welding masks. A hole can be bored into the typical mask, as indicated on FIG. 14, for the attachment. The fastener provides adequate support, although additional Velcro or other materials may be included to cause further adherence of the unit to the mask.

Increasing the resistor R2 from 150,000 ohms to 180,000 ohms allows the photovoltaic module to operate at 3.5 volts compared to 3.1 volts, which in turn causes a delivery of 12% more power under low current/low arc brightness conditions. This improves turbin start-up times and also increases the ultimate motor RPM by approximately the same factor.

The energy reservoir capacitor C1 has been reduced from 250 micro Farads to 100 micro Farads to boost the frequency of high current motor current pulses by a factor approaching 33%, thereby reducing the physical size of the capacitor.

The DC motor used for the attachable embodiment has a higher torque than that described earlier which, in turn, allows for an increase in shaft RPM speed under very high current welding arc conditions. The lower torque motor is optimal only if low current welding arcs are anticipated as in the case of hobbiest and/or consumer type welding equipment.

As indicated with the previous embodiment, the batteries are optional and, in addition, a plurality may be used in combination as deemded appropriate for the use intended.

By means of this development, it is possible for any welder to have a continuous breeze of cool, clean air without the necessity for having attached hoses or tanks in association with the welding mask. The air drawn through replaceable filters is scrubbed of ozone, smoke, gases and fumes, allowing clean, cool air to flow directly into the shield to the welder. Because of the nature of the design of the attachable unit, it mounts quickly to welding shields of all major suppliers.

The many features and advantages of the invention are apparent from the detailed specification and, thus, it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly, all suitable modifications and equivalents may be resorted to falling within the scope of the invention.

What is claimed is:

1. A photovaltaic power transmission circuit responsive to a light source, comprising:
    (A) photovoltaic power means for producing electrical energy, having a voltage, current, power, and energy capacity dependent upon light energy generated by said light source;
    (B) electrical device means for consuming the electrical energy produced by said photovaltaic power means;
    (C) switch means for connecting said electrical device means to said photovoltaic power means when said switch means is energized and for disconnecting said electrical device means from said photovoltaic power means when said switch means is de-energized;

(D) reference voltage means for outputting a reference voltage; and (E) comparing means for comparing the reference voltage with the voltage produced by said photovoltaic power means and providing first and second digital output signal states to said switching means, said first digital output signal state energizing said switch means and said second digital output signal state de-energizing said switch means.

2. A photovoltaic power transmission circuit as recited in claim 1, wherein said light source comprises an arc welder or acetylene torch flame.

3. A photovoltaic power transmission circuit as recited in claim 2, wherein said photovoltaic power means comprises:
(A) a photovaltaic panel; and
(B) a capacitor circuit coupled to said photovoltaic panel and storing voltage generated by said photovoltaic panel.

4. A photovoltaic power transmission circuit as recited in claim 3, wherein said electrical device means comprises a DC motor.

5. A photovoltaic power transmission circuit as recited in claim 4, wherein said switch means comprises a transistor for connecting and disconnecting said DC motor from said photovoltaic power means.

6. A photovoltaic power transmission circuit as recited in claim 5, wherein said comparing means comprises:
(A) a comparator; and
(B) a voltage divider coupled between said comparator and said photovoltaic power means.

7. A welder's helmet comprising in combination:
(A) a viewing window in the front of said helmet;
(B) a protective shield disposed in front of the said viewing window;
(C) a photovoltaic generator device carried by said helmet at a position vertically above or below said viewing window;
(D) a protective shield disposed in front of the said photovoltaic generator device;
(E) a photovoltaic power transmission circuit responsive to a light source, comprising:
  (a) photovoltaic power means of producing electrical energy, having a voltage, current, power and energy capacity dependent upon light energy generated by said light source;
  (b) electrical device means for consuming the electrical energy produced by said photovoltaic power means;
  (c) switch means for connecting said electrical device means to said photovoltaic power means when said switch means is energized and for disconnecting said electrical device means from said photovoltaic power means when said switch means is de-energized;
  (d) reference voltage means for outputting a reference voltage; and
  (e) comparing means for comparing the reference voltage with the voltage produced by said photovolacid power means and providing first and second digital output signal states to said switching means, said first signal digital output signal state energizing said switch means and said second digital output signal state de-energizing said switch means;
(F) an electrically driven airstream generated carried by and within said helmet to draw air into said helmet through suitable filtering means and to distribute the filtered air throughout said helmet; and
(G) means electrically connecting said transmission circuit to said air stream generator.

8. An air filtering unit attachable to a welder'helmet comprising in combination:
(A) a photovoltaic generator device;
(B) a protective shield disposed in front of the said photovoltaic generator device;
(C) a photovaltaic power transmission circuit responsive to a light source, comprising:
  (a) photovoltaic power means for producing electrical energy, having a voltage, current, power and energy capacity dependent upon light energy generated by said light source;
  (b) electrical device means for consuming the electrical energy produced by said photovoltaic power means;
  (c) switch means for connecting said electrical device means to said photovoltaic power means when said switch means is energized and for disconnecting said electrical device means from said photovoltaic power means when said switch means is de-energized;
  (d) reference voltage means for outputting a reference voltage; and
  (e) comparing means for comparing the reference voltage with the voltage produced by said photovoltaic power means and providing first and second digital output signal states to said switching means, said first signal digital output state energizing said switch means and said second digital output signal state de-energizing said switch means;
(D) an electrical driven airstream generated carried by and within said attachable unit to draw air into said unit through suitable filtering means and to discharge the filtered air throughout a conduit means;
(E) means electrically connecting said transmission circuit to said airstream generator; and (F) means for connecting and attaching said attachable unit to a welding mask with said conduit means passing through an opening in said welding mask and with said photoelectric generator device oriented in the same general direction as the viewing glass of the welding mask.

* * * * *